(12) United States Patent
Zhou

(10) Patent No.: US 11,540,942 B2
(45) Date of Patent: Jan. 3, 2023

(54) REDUNDANT PNEUMATIC CIRCUIT FOR RELIABILITY ENHANCEMENT OF VITRECTOMY INSTRUMENTS

(71) Applicant: Alcon Inc., Fribourg (CH)

(72) Inventor: Jiansheng Zhou, Cerritos, CA (US)

(73) Assignee: Alcon Inc., Fribourg (CH)

( * ) Notice: Subject to any disclaimer, the term of this patent is extended or adjusted under 35 U.S.C. 154(b) by 790 days.

(21) Appl. No.: 16/511,950

(22) Filed: Jul. 15, 2019

(65) Prior Publication Data

US 2020/0030149 A1 Jan. 30, 2020

Related U.S. Application Data

(60) Provisional application No. 62/703,557, filed on Jul. 26, 2018.

(51) Int. Cl.
| | | |
|---|---|---|
| *A61F 9/007* | (2006.01) | |
| *A61B 34/00* | (2016.01) | |
| *A61B 5/06* | (2006.01) | |
| *F15B 19/00* | (2006.01) | |
| *G05D 16/00* | (2006.01) | |
| *G05D 16/20* | (2006.01) | |
| *A61B 17/00* | (2006.01) | |
| *F15B 20/00* | (2006.01) | |

(52) U.S. Cl.
CPC .......... *A61F 9/00763* (2013.01); *A61B 5/061* (2013.01); *A61B 34/25* (2016.02); *F15B 19/005* (2013.01); *G05D 16/028* (2019.01); *A61B 2017/00017* (2013.01); *A61B 2017/00119* (2013.01); *A61B 2017/00544* (2013.01); *F15B 20/008* (2013.01); *F15B 2211/327* (2013.01); *F15B 2211/6313* (2013.01); *F15B 2211/7053* (2013.01); *F15B 2211/8636* (2013.01); *G05D 16/2006* (2013.01); *Y10T 137/2554* (2015.04)

(58) Field of Classification Search
CPC .......... Y10T 137/2554; A61F 9/00763; A61B 34/25; A61B 5/061; A61B 2017/00017; A61B 2017/00119; A61B 2017/00544; G05D 16/028; G05D 16/2006; F15B 19/005; F15B 2211/327; F15B 2211/328; F15B 2211/6313; F15B 2211/7053; F15B 2211/8636; F15B 2211/867; F15B 2211/8855; F15B 20/008
See application file for complete search history.

(56) References Cited

U.S. PATENT DOCUMENTS

| | | | | |
|---|---|---|---|---|
| 3,680,583 | A * | 8/1972 | Clair | F16K 11/0704 91/356 |
| 3,874,269 | A * | 4/1975 | Walters | F15B 13/0417 91/451 |
| 4,008,875 | A * | 2/1977 | Olson | B66F 9/183 251/63.4 |
| 4,300,584 | A * | 11/1981 | Kosarzecki | F15B 11/15 91/356 |
| 4,462,418 | A * | 7/1984 | Xander | F15B 21/02 137/624.14 |
| 4,749,055 | A * | 6/1988 | Momiyama | B62D 5/087 60/426 |

(Continued)

*Primary Examiner* — William M McCalister

(57) ABSTRACT

Systems, methods, and computer-readable media for enhancing the reliability of a pneumatically driven surgical tool by providing a redundant, backup pneumatic circuit for supplying the surgical tool with pneumatic pressure at a normal pressure.

20 Claims, 10 Drawing Sheets

Vitrectomy Pneumatic Module - Primary Circuit Operation

(56) References Cited

U.S. PATENT DOCUMENTS

| | | |
|---|---|---|
| 4,770,654 A | 9/1988 | Rogers et al. |
| 4,810,242 A | 3/1989 | Sundblom |
| 4,914,913 A * | 4/1990 | St. Germain ............ B62D 5/09 |
| | | 60/462 |
| 8,162,000 B2 | 4/2012 | Turner |
| 8,312,800 B2 | 11/2012 | Turner |
| 8,728,108 B2 | 5/2014 | Gao |
| 8,818,564 B2 | 8/2014 | Zhou |
| 8,821,524 B2 | 9/2014 | Agahi |
| 9,180,049 B2 | 11/2015 | Underwood |
| 9,241,830 B2 | 1/2016 | Olivera |
| 9,326,826 B2 | 5/2016 | Turner |
| 9,924,963 B2 | 3/2018 | Mcdonell |
| 10,070,990 B2 | 9/2018 | Mcdonell |
| 2010/0065135 A1* | 3/2010 | Rub ...................... F15B 21/047 |
| | | 137/528 |
| 2011/0083750 A1* | 4/2011 | Gehlhoff ............... F15B 20/002 |
| | | 137/12 |
| 2013/0144317 A1* | 6/2013 | Valencia ............. A61F 9/00763 |
| | | 606/170 |
| 2015/0153081 A1* | 6/2015 | Gurley ................ F16K 99/0011 |
| | | 137/106 |
| 2017/0087283 A1* | 3/2017 | Ovchinnikov ...... A61F 9/00745 |
| 2019/0183679 A1 | 6/2019 | Sawicz |
| 2020/0030149 A1* | 1/2020 | Zhou ................... G05D 16/028 |
| 2020/0179169 A1* | 6/2020 | Agahi ................ F16K 37/0041 |
| 2020/0340600 A1* | 10/2020 | Zhou .................. A61F 9/00745 |

* cited by examiner

REDUNDANT PNEUMATIC CIRCUIT FOR RELIABILITY ENHANCEMENT OF VITRECTOMY INSTRUMENTS

PRIORITY CLAIM

This application claims the benefit of priority of U.S. Provisional Patent Application Ser. No. 62/703,557 titled "Redundant Pneumatic Circuit for Reliability Enhancement of Vitrectomy Instruments," filed on Jul. 26, 2018, whose inventor is Jiansheng Zhou, which is hereby incorporated by reference in its entirety as though fully and completely set forth herein.

BACKGROUND

Field of the Disclosure

The present disclosure relates to a pneumatic circuit and, more specifically, to a redundant pneumatic circuit for supplying a surgical tool with pneumatic pressure.

Description of Related Art

Vitreo-retinal procedures may include a variety of surgical procedures performed to restore, preserve, and enhance vision. Vitreo-retinal procedures may be appropriate to treat many serious conditions of the back of the eye. Vitreo-retinal procedures may treat conditions such as age-related macular degeneration (AMD), diabetic retinopathy and diabetic vitreous hemorrhage, macular hole, retinal detachment, epiretinal membrane, CMV retinitis, and many other ophthalmic conditions.

The vitreous is a normally clear, gel-like substance that fills the center of the eye. It may make up approximately ⅔ of the eye's volume, giving it form and shape before birth. Certain problems affecting the back of the eye may require a vitrectomy, or surgical removal of the vitreous. Removal of vitreous can involve a vitrector, or cutting device, that works like a tiny guillotine, with an oscillating microscopic cutter to remove the vitreous gel in a controlled fashion. Operating the cutter at a high cut rate may prevent significant traction on the retina during the removal of the vitreous humor. Also, the cutter can be driven by pneumatic module that may condition and supply compressed air or gas to power the cutter.

SUMMARY

The disclosed embodiments of the present technology relate to systems, methods, and computer-readable media for enhancing the reliability of a pneumatically driven surgical tool by providing a redundant, backup pneumatic circuit for supplying the surgical tool with pneumatic pressure at a normal pressure.

Some embodiments of the present technology involve a source of regulated pneumatic pressure and a redundant pneumatic circuit that includes an isolation valve fluidly coupled to the source of regulated pneumatic pressure and fluidly coupled to both a primary drive valve and a backup drive valve.

The redundant pneumatic circuit can also include a first circuit selection valve and a second circuit selection valve, each coupled with a respective first and second chamber of a surgical tool and coupled with both the primary drive valve and the backup drive valve. When the redundant pneumatic circuit is in a primary drive mode, the isolation valve is positioned to allow pneumatic pressure to flow to the primary drive valve and suppress pneumatic pressure to the backup drive valve. Also, the circuit selection valves are positioned to receive pneumatic pressure from the primary drive valve and to alternatively drive and vent the first chamber and the second chamber of the surgical tool.

A diaphragm connected to a cutting device separates the first chamber and the second chamber of the surgical tool. The cutting device performs a cutting function when the diaphragm is actuated by pneumatic pressure alternatively driving and venting the first chamber and the second chamber.

The redundant pneumatic circuit can also include a first and second pressure sensor respectively positioned between the first circuit selection valve and the second circuit selection valve and the respective chambers of the surgical tool. The pressure sensors can be communicatively coupled with a control system containing a processor which can monitor the pneumatic pressure from the first pressure sensor and the second pressure sensor and determine when the pneumatic pressure flowing through the first pressure sensor and the second pressure sensor is normal or abnormal. In some cases, the processor determines that the pneumatic pressure flowing through the first pressure sensor and the second pressure sensor is abnormal by determining when differential pressure between the first pressure sensor and the second pressure sensor is below a threshold value.

When the pressure delivered to the chambers is determined to be abnormal, the processor can switch to the backup pneumatic circuit by actuating the isolation valve to suppress pneumatic pressure to flow to the primary drive valve and allow pneumatic pressure to the backup drive valve. Likewise, the circuit selection valves are actuated to receive pneumatic pressure from the backup drive valve and to alternatively drive and vent the first chamber and the second chamber of the surgical tool.

Before switching to the backup drive valve, the system controller can also apply a remediation step in an attempt to return the differential pressure between the first pressure sensor and the second pressure sensor to exceed a threshold value. The remediation step can involve adjusting a valve duty cycle of the primary drive valve. The remediation step can also be performed after switching to the backup drive valve. In this case, if the remediation step is unsuccessful, the operation can be terminated.

Some embodiments of the present technology also involve a method of enhancing the reliability of a pneumatically driven surgical tool. The method can include monitoring, the pneumatic pressure of a first circuit selection valve and second circuit selection valve coupled with a respective first and second chamber of a surgical tool and respectively coupled with both a primary drive valve and a backup drive valve. The method can also include determining that the pneumatic pressure flowing through one or both of the first fluidic line and the second fluidic line is abnormal and determining to switch to a backup drive valve mode by actuating an isolation valve to suppress pneumatic pressure flowing to the primary drive valve and allowing the pneumatic pressure to flow to the backup drive valve and actuating the first and second circuit selection valves to selectively receive pneumatic pressure from the backup drive valve and to alternatively drive and vent the first chamber and the second chamber of a surgical tool.

In some cases, after determining that the pneumatic pressure flowing through one or both of the first fluidic line and the second fluidic line is abnormal and before actuating the isolation valve and the first and second circuit selection valves, applying a remediation step to return the differential pressure between the first pressure sensor and the second pressure sensor to exceed a threshold value.

BRIEF DESCRIPTION OF THE DRAWINGS

For a more complete understanding of the present technology, its features, and its advantages, reference is made to the following description, taken in conjunction with the accompanying drawings, in which.

DESCRIPTION

The disclosed embodiments of the present technology relate to systems, methods, and computer-readable media for enhancing the reliability of a pneumatically driven surgical tool by providing a redundant, backup pneumatic circuit for supplying the surgical tool with pneumatic pressure at a normal pressure.

Figure 1:
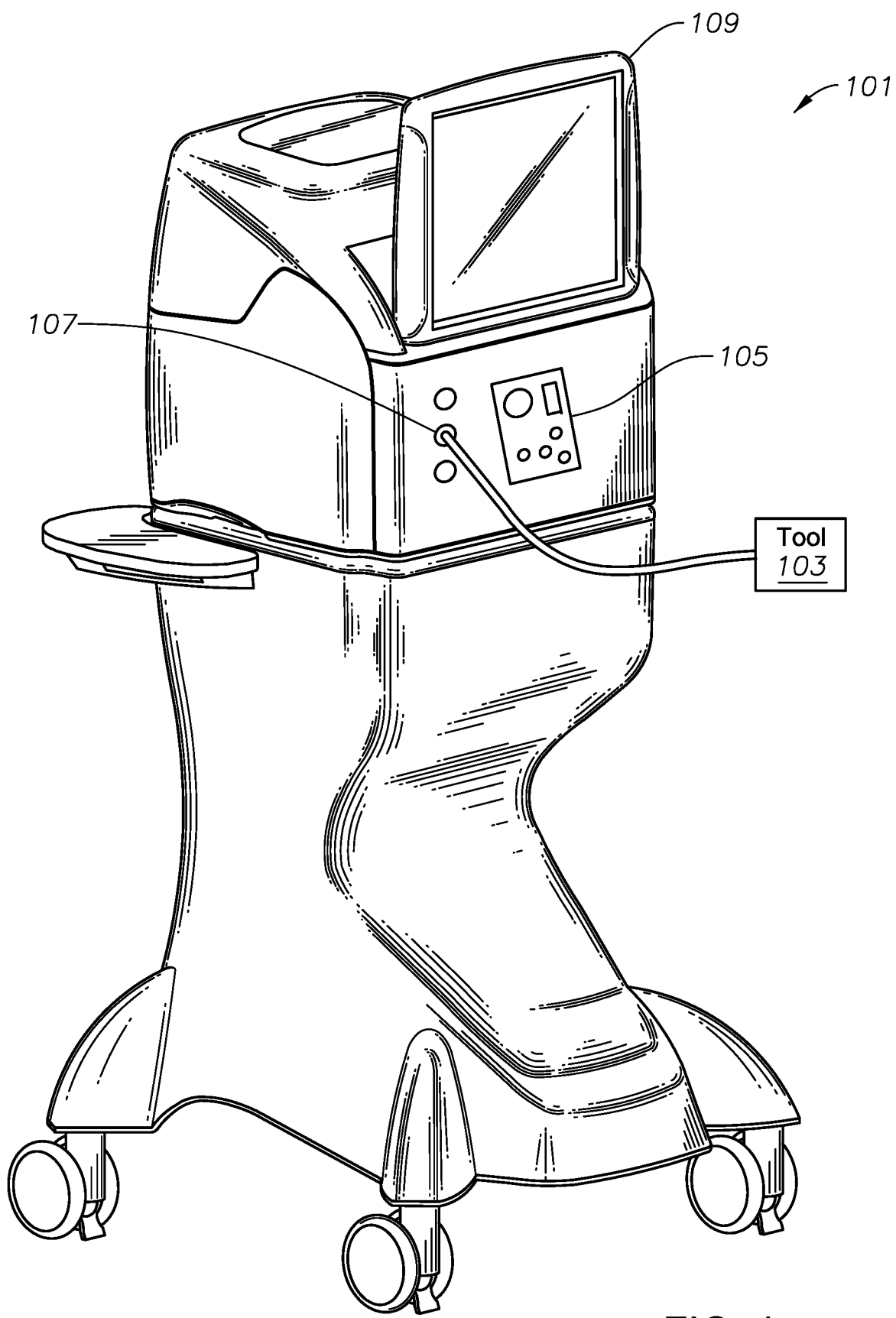
FIG. 1 illustrates an embodiment of a surgical console 101 for a pneumatically powered ophthalmic surgical machine.

FIG. 1 illustrates an embodiment of a surgical console 101 for a pneumatically powered ophthalmic surgical machine. The surgical console 101 may be configured to drive one or more pneumatic tools 103. The tools 103 may include, for example, scissors, vitrectors, forceps, and injection or extraction modules. Other tools 103 may also be used. In operation, the pneumatically powered ophthalmic surgery machine of FIG. 1 may operate to assist a surgeon in performing various ophthalmic surgical procedures, such as a vitrectomy. A compressed gas, such as nitrogen, may provide the power through the surgical console 101 to power tools 103. The surgical console 101 may include a display 109 for displaying information to a user (the display may also incorporate a touchscreen for receiving user input). The surgical console 101 may also include a fluidics module 105 (e.g., to support irrigation/aspiration functions) and one or more port connectors 107 for coupling to tools 103 (e.g., coupling through pneumatic lines attached to the tools 103).

Figure 2A:
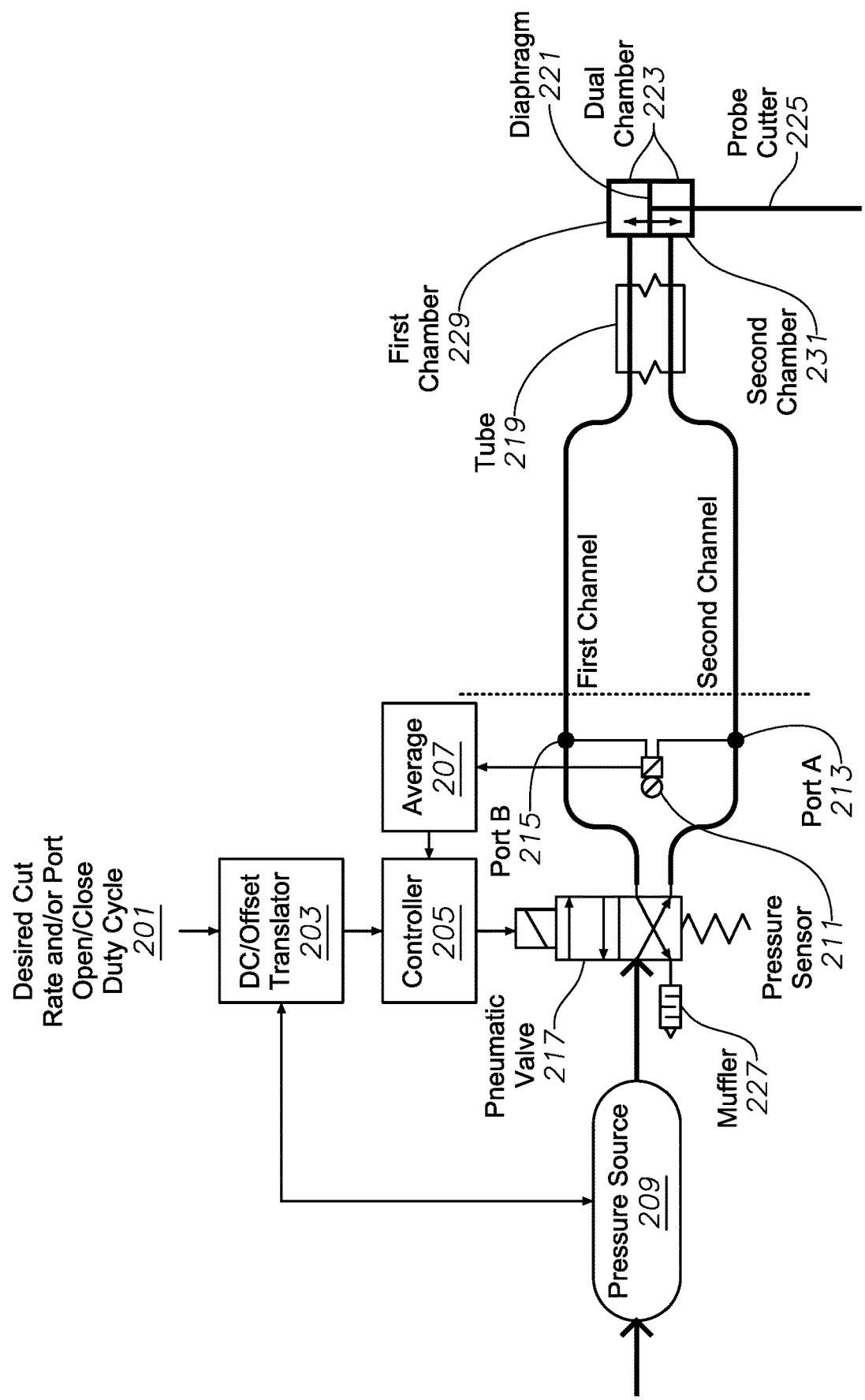
FIGS. 2A and 2B illustrate a schematic of a pneumatic system for a pneumatically powered vitrectomy machine.
Figure 2B:
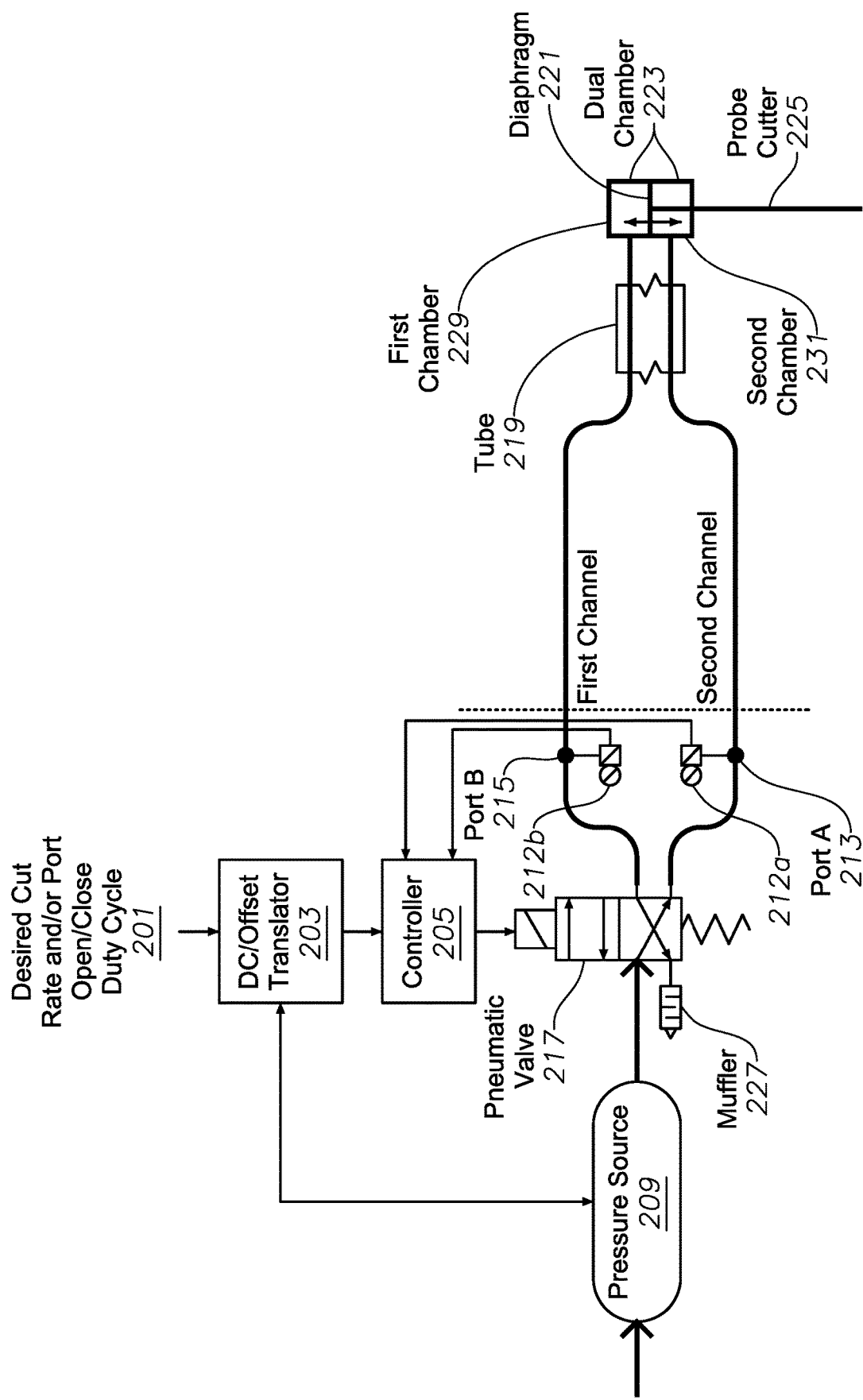

FIGS. 2A and 2B illustrate a schematic of a pneumatic system for a pneumatically powered vitrectomy machine. As seen in FIGS. 2A and 2B, the pneumatic system may include one or more pneumatic valves 217 coupling a pressure source 209 (e.g., a regulated pressure source such as an air cylinder or a wall outlet air supply) to output port A 213 and output port B 215 (the output port A 213 and output port B 215 may be coupled to the tool 103 through one or more port connectors 107). In some embodiments, the pneumatic valve 217 may be controlled by controller 205. In some embodiments, the pressure of the pressure source 209 may also be regulated by controller 205 or a separate controller (e.g., internal to the surgical console 101). The controller 205 may regulate pressure (e.g., to balance between lower pressures for reducing air consumption and higher pressures for faster cut rates and/or to increase a dynamic range of available cut rates). In some embodiments, the components of the pneumatic system may be incorporated in a manifold (e.g., machined out of a metal, such as aluminum). The manifold may be air tight, and include various fittings and couplings, and be capable of withstanding relatively high gas pressures. The manifolds may be manufactured as individual pieces or they may be manufactured as a single piece. In various embodiments, the components of the pneumatic system (e.g., in the manifold) may be incorporated inside the surgical console 101.

The valve 217 may include a solenoid that operates to move the valve 217 to one of the two positions (e.g., see FIGS. 2 a-b) as directed by control signals from controller 205. In a first position, pneumatic valve 217 may allow pressurized gas to pass through pneumatic valve 217 to output port B 215 to provide pneumatic power to the probe cutter 225 while venting pressurized gas from output port A 213 through muffler 227. In a second position, the valve 217 may provide pressurized gas to output port A 213 and vent pressurized gas from output port B 215. In this position, pressurized gas may pass through output port A 213 to provide pneumatic power to a tool 103 (e.g., probe cutter 225). Thus, when the pneumatic valve 217 is in the first position, the first chamber 229 of the dual chambers 223 may be charged while the second chamber 231 may be discharged. When the pneumatic valve 217 is in the second position the second chamber 231 may be charged while the first chamber 229 may be discharged.

Figure 3:
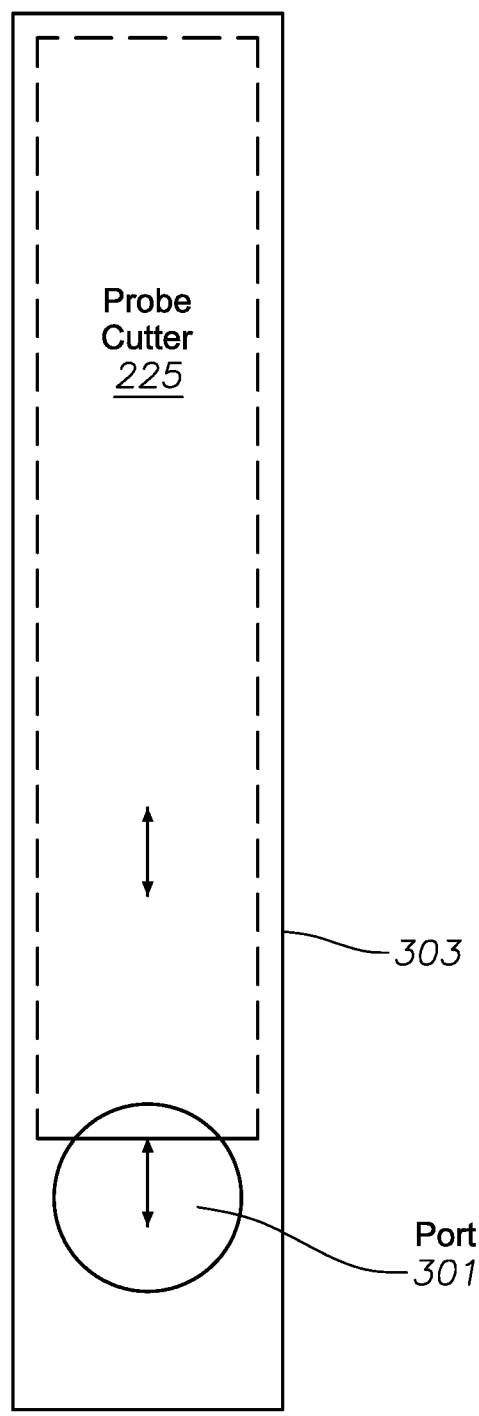
FIG. 3 illustrates the cutting device of a surgical probe.

As seen in FIG. 3, the probe cutter 225 may act as a cutting device. The probe cutter 225 may reciprocate inside an outer tube 303 with a cutter port 301 (e.g., the probe cutter 225 may be moved by a diaphragm 221 that in turn oscillates as pressurized gas is alternately directed to output ports A and B (and into respective chambers of the dual chamber 223)). In some embodiments, probe cutter 225 may be attached to output ports A and B through tube 219 (separate tubes for each port may also be used). As the probe cutter 225 moves back and forth, the probe cutter 225 may alternately open and close cutter port 301 with a sharpened tip of the probe cutter 225. Each cycle of the probe cutter 225 through outer tube 303 may cut through material such as vitreous in the cutter port 301 as the probe cutter 225 is closing. A port duty cycle (PDC) may indicate the amount of time the cutter port 301 is open and closed. For example, a PDC of 49% may indicate the cutter port 301 is open 49% of the cycle time (and closed 51% of the cycle time—the cycle time being, for example, the amount of time between each successive opening of the cutter port 301).

In some embodiments, the valve duty cycle (VDC) may include the amount of time the pneumatic valve 217 is in the first and second positions. In some embodiments, a cut rate of the probe cutter 225 may be controlled by the controller 205 through valve 217. For example, to provide a 2500 cuts per minute probe rate, controller 205 may direct pneumatic valve 217 to provide pressurized air alternately to port A (second channel) and port B (first channel) at a rate of approximately 24 ms per cycle. To obtain a cut rate of 2500 cuts per minute, the two pneumatic channels may cycle open/closed every 24 ms (2500 cuts/min or 1 min/2500 cuts*60 seconds/1 min=0.024 seconds/cut=24 ms/cut), which may open for 12 ms to each channel.

For the benefit of reducing traction (which can cause retinal detachment) during vitrectomy procedure, the vitrectomy probe is desired to be operated at high speed. The common understanding is the faster the better. Therefore the drive valve is often operated at its maximum speed (in CPM). At very high speed, each valve cycle time is very short, which requires the solenoid valve to move very fast in opening and closing. For example, at 15,000 cpm with 50%

VDC, in each valve cycle the time duration of valve open and close is only 2 ms. Therefore the solenoid valve has to actuate very fast so that it opens and closes in less than 2 ms.

In some cases, increasing solenoid power by coil design and/or applying higher voltage along with stronger return spring can speed up the valve actuation. However, increasing speed can reduce the reliability of the drive valve because the number of valve cycle increases in a given time and valve operating condition is worsened at higher speed due to higher mechanical impact and heat. In other words, the usage life of the drive valve can be reduced when it is operated at higher speed (in CPM). When the drive valve fails or malfunctions, the vitrectomy instrument effectively ceases to function. In this case, the vitrectomy procedure will have to be terminated, which could become an adverse event.

Figure 4A:
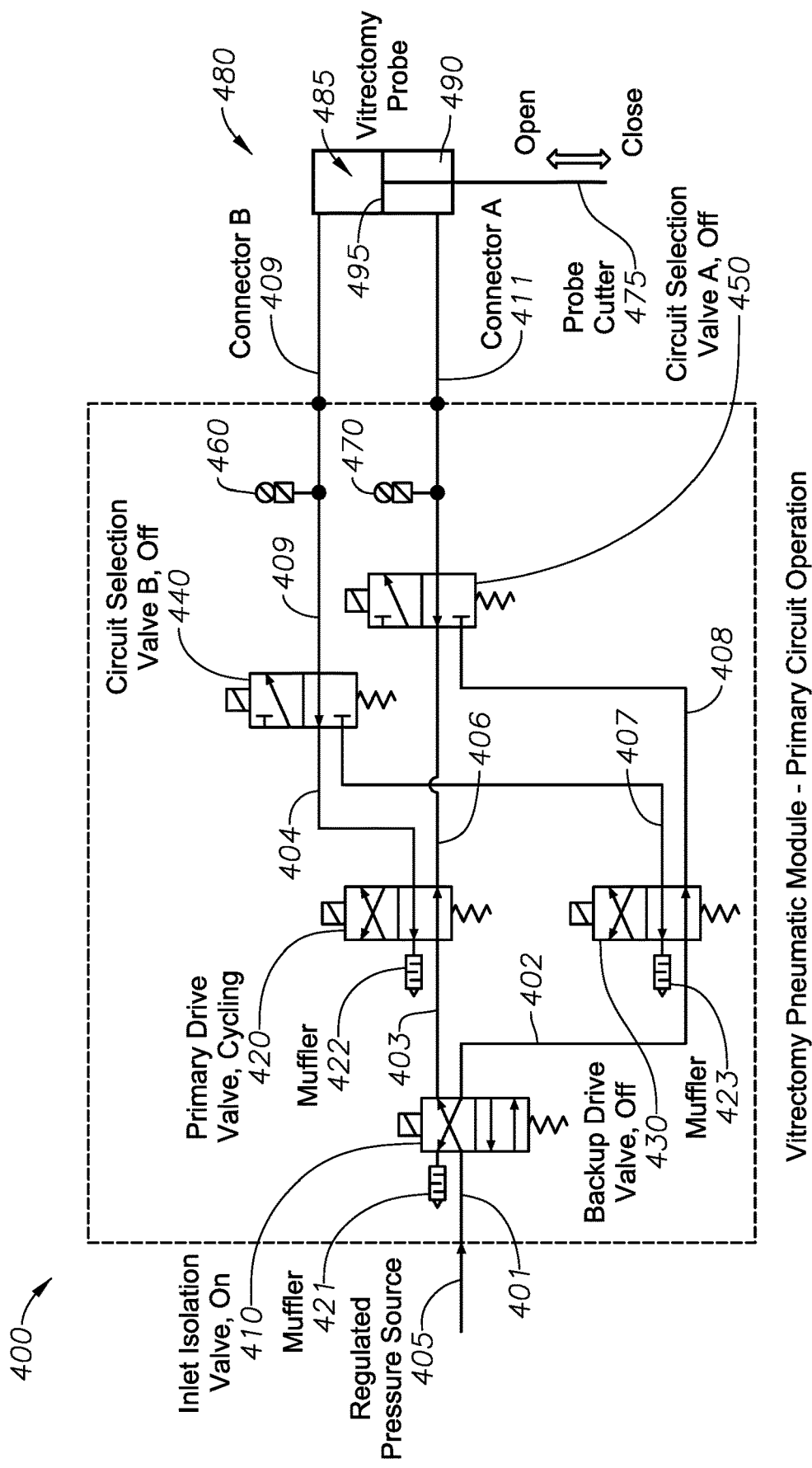
FIGS. 4A and 4B illustrates a redundant pneumatic circuit in a primary mode and a backup mode respectively.

To enhance reliability of vitrectomy instruments, the present technology incorporates a redundant pneumatic circuit in the pneumatic circuit design. When primary drive valve fails or malfunctions, the system automatically switches to backup pneumatic circuit, which operates the backup drive valve instead. FIG. 4A illustrates a redundant pneumatic circuitry 400 including a primary drive valve 420 in operation and a backup drive valve 430 that can be engaged to power a vitrectomy probe 480 when the primary drive valve 420 fails. The redundant pneumatic circuitry 400 includes a source of regulated pneumatic pressure 405 (e.g. compressed air canister, hospital wall air, etc.) and tubing 401, 402, 403, 404, 406, 407, 408, 409, 411 for fluidly coupling the components of the redundant pneumatic circuitry 400 with the vitrectomy probe 480.

The source of regulated pneumatic pressure 405 is fluidly coupled with an isolation valve 410 via tubing 401. As shown in FIG. 4A, the isolation valve 410 is a four-way valve. The isolation valve 410 is fluidly coupled (via tubing 402, 403) to a primary drive valve 420 and a backup drive valve 430. Also, each of the primary drive valve 420 and a backup drive valve 430 are fluidly coupled (via tubing 404, 406, 407, 408) to both of a first circuit selection valve 440 and a second circuit selection valve 450.

The first circuit selection valve 440 and a second circuit selection valve 450 are respectively coupled (via tubing 409, 411) to a first chamber 485 and a second chamber 490 of the vitrectomy probe 480. The first chamber 485 and the second chamber 490 are separated by a diaphragm 495 which is alternatively displaced when one of the primary drive valve 420 or the backup drive valve 430 alternatively drive and vent the chambers 485, 490. The diaphragm 495, in turn, drives the probe cutter 475 in a manner described above. The redundant pneumatic circuitry 400 can also include one or more mufflers 421, 422, 423 to suppress acoustic noise that results from the valves venting the pressurized fluid to atmosphere.

In this detailed description, the terms "off" and "on" in the context of the valves state are used as a convenience; however, the description of the valve states as "on" and "off" should not be read to imply functionality, non-functionality, etc.

Prior to a vitrectomy procedure, the isolation valve 410, the first circuit selection valve 440, and the second circuit selection valve 450 are all in an "off" state. When these valves are in an "off" state, the flow of the pneumatic pressure is suppressed from being delivered to the vitrectomy probe 480 by virtue of the isolation valve 430 delivering the pneumatic pressure through the backup drive valve 430 and to the first and second circuit selection valves 440, 450, which block the flow of fluid in their "off" state.

At the initiation of a vitrectomy procedure, the inlet isolation valve is actuated and put into an "on" state, which supplies pneumatic flow and pressure to the primary drive valve 420. The primary drive valve 420 cycles on/off at a specific rate (i.e. cuts per minute or CPM) and with specific valve duty cycle (VDC) determined by the user and system control software. The first and second circuit selection valves 440, 450 remain in their "off" state, which allow pneumatic flow and pressure from the primary drive valve 420 to go through the first and second circuit selection valves 440, 450 and to respective chambers 485, 490 of the vitrectomy probe 480 and causes the probe cutter 475 to cut at the specified CPM.

The redundant circuitry 400 also include two pressure sensors 460, 470 and one or more system controllers (not shown). The pressure sensors 460, 470 monitor pressure of the two channels of tubing 409, 411 in real time and the system controller receives and processes the pressure data in real time. The system controller can determine when the pressure is normal or abnormal by a variety of methods. For example, in some cases, the system controller can determine whether or not the pressure is normal by examining a differential pressure between channels monitored by the two pressure sensors 460, 470.

Figure 5:
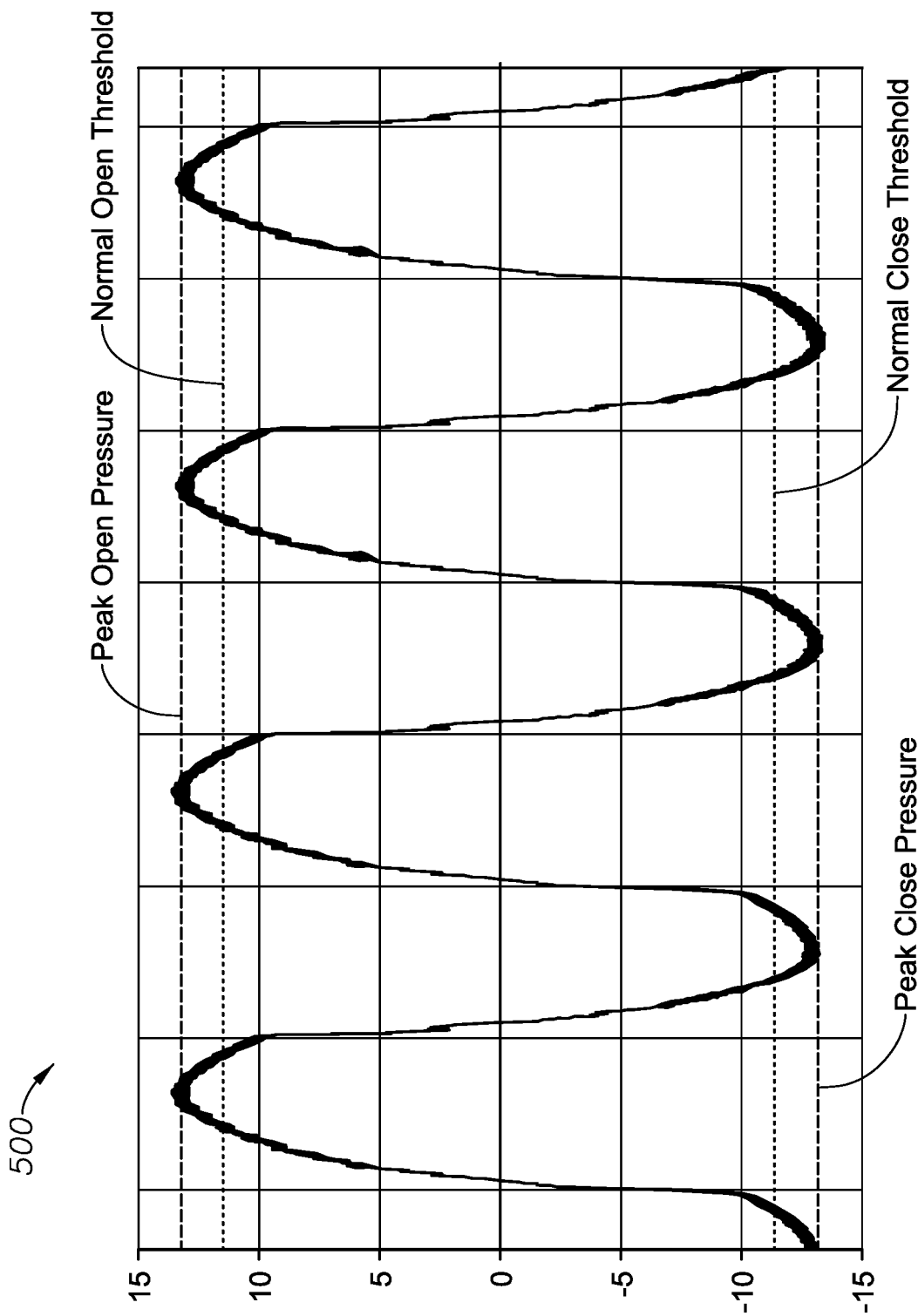
FIG. 5 illustrates an example of a plot showing a pressure differential over time.

FIG. 5 illustrates an example of a plot 500 showing a pressure differential over time. The system controller can examine the monitored channel pressures, calculate a differential pressure as the pressure from second pressure sensor 470 minus the pressure from the first pressure sensor 460, and report the differential pressure as being abnormal when the differential pressure exceeds a particular predetermined threshold. One particular method involves comparing peak open pressure and peak close pressure in the form of differential pressure as a second channel minus a first channel to normal open threshold and normal close threshold respectively. The system controller can report the pressure as normal when both absolute values of peak open pressure and peak close pressure are beyond the absolute values of normal open threshold and normal close threshold respectively. In this state of operation, the system controller allows the primary drive valve 420 to continue to operate.

Conversely, if the system controller determines that the pressure is abnormal, the system controller can perform one or more remediation step in an attempt to adjust the pneumatic pressure back to an acceptable level. For example, the system controller can adjust primary drive 420 valve's duty cycle (VDC) to shift the peaks of open pressure and close pressure up or down. After performing the remediation step, the system controller can examine the pneumatic pressure from the pressure sensors 460, 470 and determine if the remediation step was successful. For example, if the VDC adjustment successfully brings the absolute values of peak open pressure and peak close pressure beyond the absolute values of normal open threshold and normal close threshold respectively, the system controller determines that the remediation step was successful and causes the primary drive valve 420 to maintain operation. Conversely, when the system controller determines that the remediation step was unsuccessful, the system controller can cause the redundant circuitry 400 to switch the vitrectomy to a backup mode by switching to the backup drive valve 430.

Figure 4B:
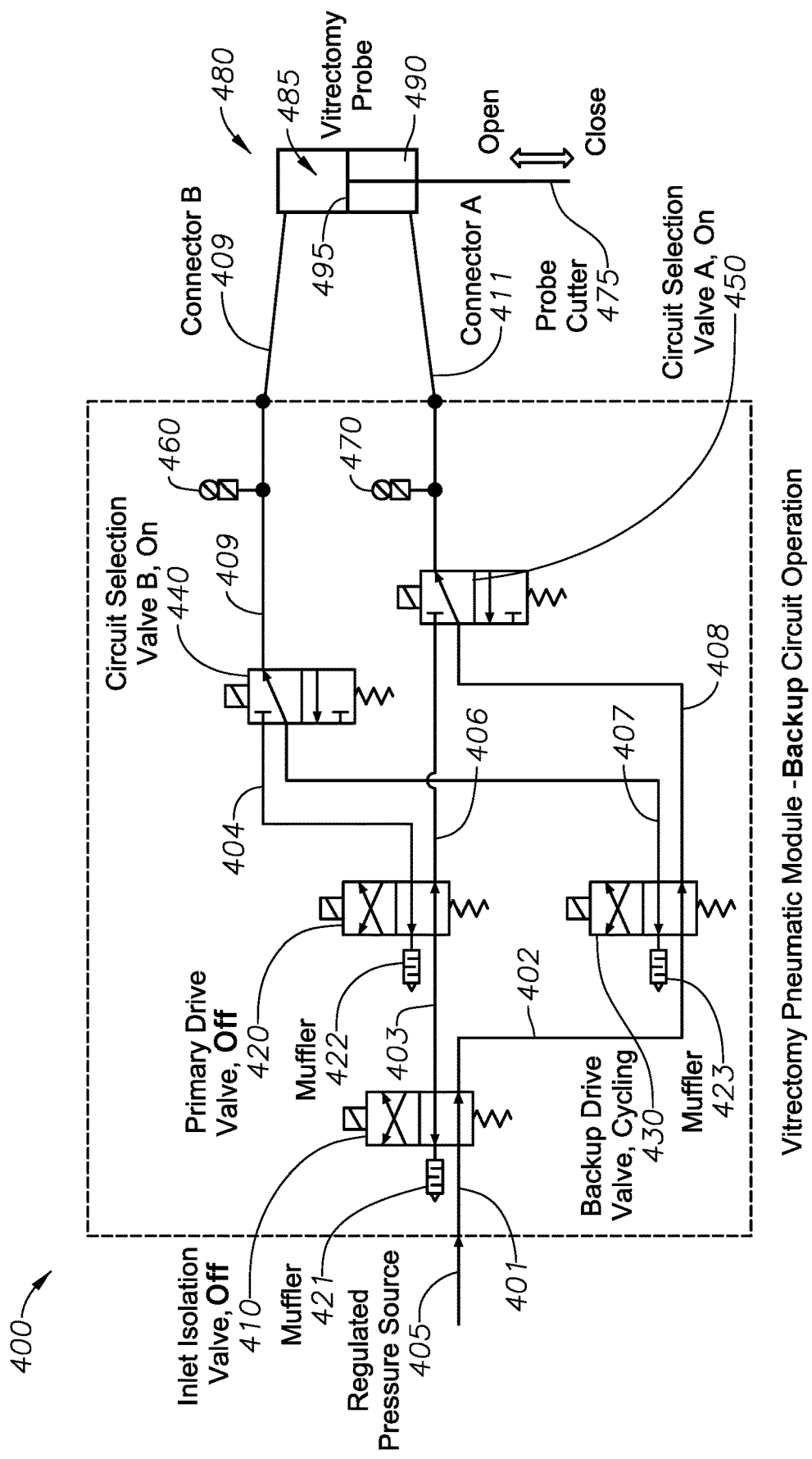

FIG. 4B illustrates the redundant pneumatic circuitry 400 with the backup drive valve 430 engaged for powering the vitrectomy probe 480 after the system controller determines that primary drive valve 420 failed. When the system controller switches the redundant pneumatic circuitry to the backup drive valve 430, the inlet isolation valve is actuated and put into an "off" state, which supplies pneumatic flow and pressure to the backup drive valve 430. The backup drive valve 430 cycles on/off at a specific rate (i.e. cuts per minute or CPM) and with specific valve duty cycle (VDC) determined by the user and system control software. Also, the system controller actuates the first and second circuit selection valves 440, 450 to their "on" state, which allow pneumatic flow and pressure from the backup drive valve 430 to go through the first and second circuit selection valves 440, 450 and to respective chambers 485, 490 of the vitrectomy probe 480 and causes the probe cutter 475 to cut at the specified CPM.

The pressure sensors 460, 470 can continue to monitor pressure of the two channels of tubing 409, 411 in real time and the system controller can continue to receive and process the pressure data in real time without interruption caused by the switch to backup mode. The system controller can determine when the pressure is normal or abnormal by a variety of methods. For example, in some cases, the system controller can determine whether the pressure is normal by examining a differential pressure between channels monitored by the two pressure sensors 460, 470.

The system controller can processes the pressure data of the two pressure sensors and determine when the pressure is normal or not, e.g. comparing peak open pressure and peak close pressure in the form of differential pressure as the second channel minus the first channel to normal open threshold and normal close threshold respectively. When the pressure is normal, the system controller can cause the backup drive valve 430 to continue to operate. When the pressure is abnormal, the system controller can perform another remediation step, e.g. adjusting backup drive 430 valve's duty cycle (VDC) to shift the peaks of open and close pressure up or down. When the remediation step is successful in bringing the pressure back to normal, the system controller can cause the backup drive valve 430 to maintain operation. When the remediation step is unsuccessful in bringing the pressure back to normal, the system controller can determine that an unresolvable system fault has occurred, and the system controller can shut down vitrectomy operation.

In some cases, whenever the backup drive valve 430 is switched on, the system controller will notify the user. For example, the system controller can notify the user to contact a service representative. In some cases, the system controller can automatically notify a service representative, order replacement parts, schedule a service appointment, etc.

In addition, since the backup drive valve 430 maintains the same vitrectomy operation as the primary drive valve 420, the vitrectomy procedure is not interrupted or stopped and the service to resolve the primary drive valve 420 failure or malfunction is not urgent.

Figure 6:
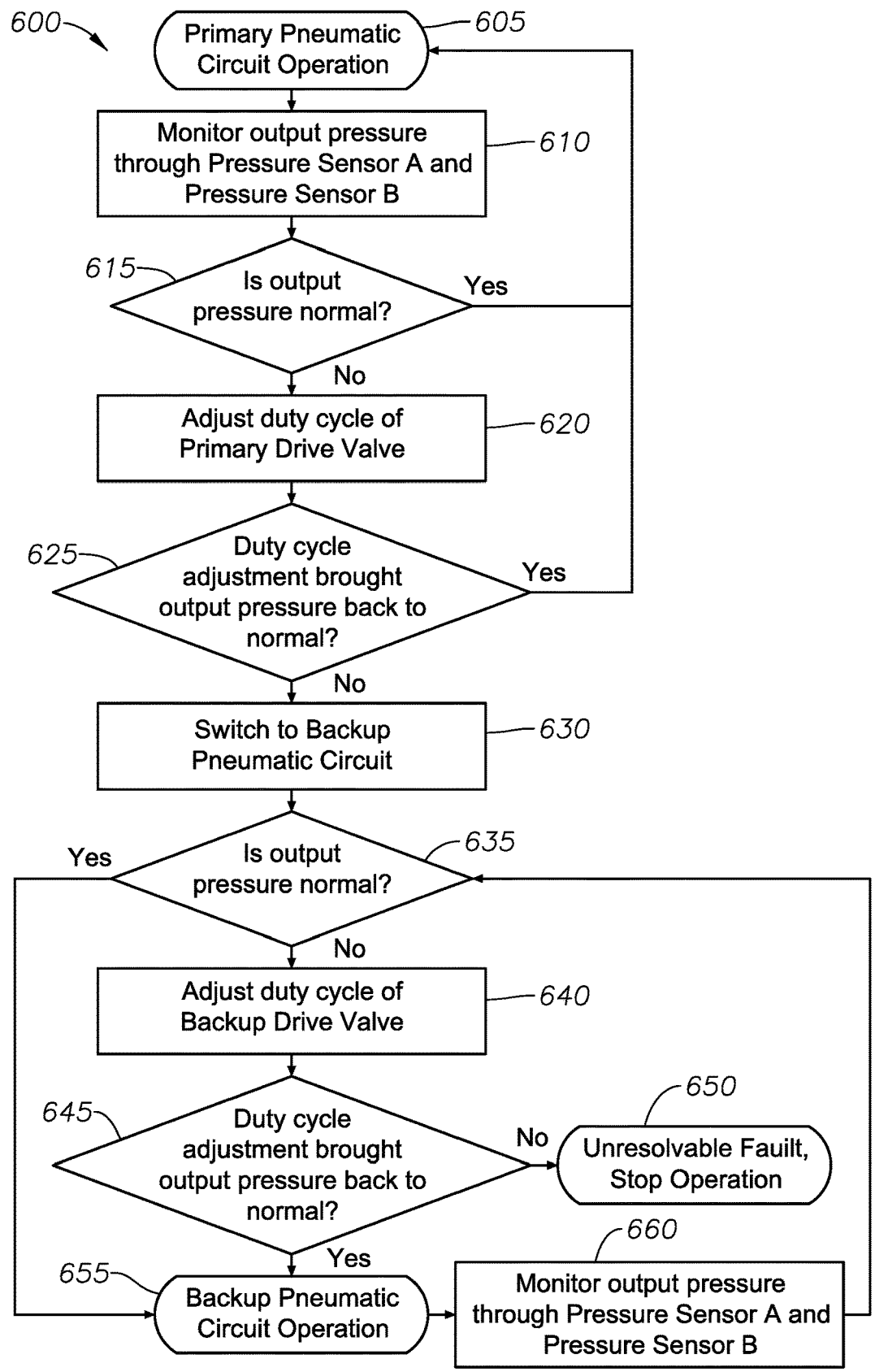
FIG. 6 illustrates a method of redundant pneumatic circuitry operation.

FIG. 6 illustrates a method 600 of redundant pneumatic circuitry operation according to some embodiments of the present technology. The method 600 involves operating a primary pneumatic drive valve circuit 605, monitoring the output pressure 610 through a first pressure sensor and a second pressure sensor, and determining whether the output pressure is normal 615. When the output pressure is normal, the method 600 involves iterating to operating a primary pneumatic drive valve circuit 605. When the output pressure is abnormal, the method 600 involves taking a remediation action by adjusting the duty cycle of the primary drive valve 620.

Next, the method 600 involves determining whether the duty cycle adjustment brought the output pressure back to normal 625. When the duty cycle adjustment remediates the abnormal pressure output, the method 600 involves iterating to operating a primary pneumatic drive valve circuit 605. On the other hand, when the duty cycle adjustment does not remediate the abnormal pressure output, the method 600 involves switching to operation with a backup pneumatic drive valve circuit 630.

After switching to a backup pneumatic drive valve circuit, the method 600 involves determining whether the output pressure is normal 635. When the output pressure is normal, the method 600 involves iterating to operating with the backup pneumatic drive valve circuit 655 and monitoring the output pressure 660 through a first pressure sensor and a second pressure sensor. When the output pressure is abnormal, the method 600 involves taking another remediation action by adjusting the duty cycle of the primary drive valve 640.

Next, the method 600 involves determining whether the duty cycle adjustment brought the output pressure back to normal 645. When the duty cycle adjustment remediates the abnormal pressure output, the method 600 involves iterating to operating with the backup pneumatic drive valve circuit 655 and monitoring the output pressure 660 through a first pressure sensor and a second pressure sensor. On the other hand, when the duty cycle adjustment does not remediate the abnormal pressure output, the method 600 involves identifying an unresolvable fault and stopping the operation 650.

Figure 7A:
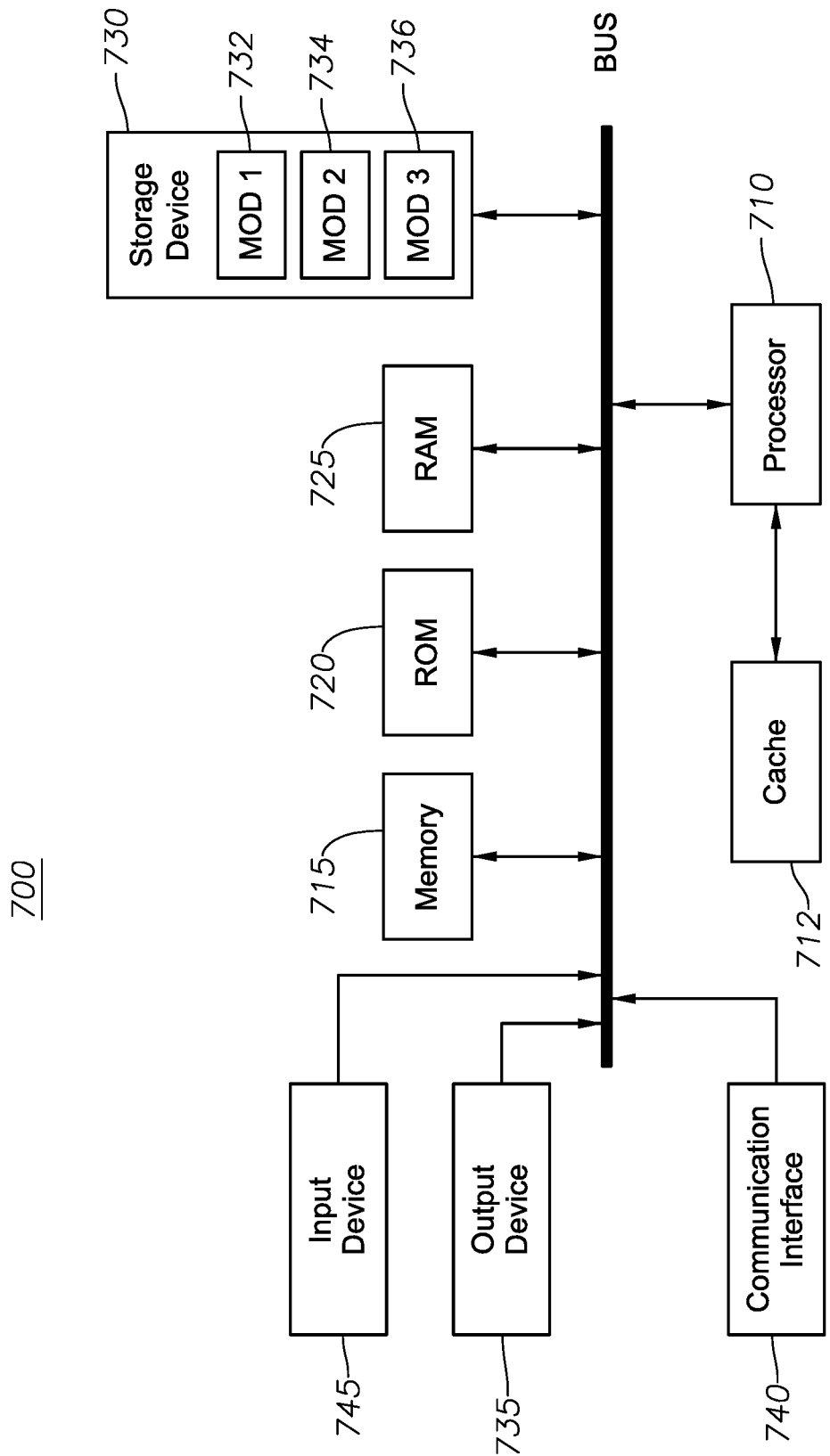
FIGS. 7A and 7B illustrate possible system embodiments.

FIG. 7A illustrates a conventional system bus computing system architecture 1000 wherein the components of the system are in electrical communication with each other using a bus 705. Exemplary system 700 includes a processing unit (CPU or processor) 710 and a system bus 705 that couples various system components including the system memory 715, such as read only memory (ROM) 720 and random access memory (RAM) 725, to the processor 710. The system 700 can include a cache of high-speed memory connected directly with, in close proximity to, or integrated as part of the processor 710. The system 700 can copy data from the memory 715 and/or the storage device 730 to the cache 712 for quick access by the processor 710. In this way, the cache can provide a performance boost that avoids processor 710 delays while waiting for data. These and other modules can control or be configured to control the processor 710 to perform various actions. Other system memory 715 may be available for use as well. The memory 715 can include multiple different types of memory with different performance characteristics. The processor 710 can include any general purpose processor and a hardware module or software module, such as module 1 732, module 2 734, and module 3 736 stored in storage device 730, configured to control the processor 710 as well as a special-purpose processor where software instructions are incorporated into the actual processor design. The processor 710 may essentially be a completely self-contained computing system, containing multiple cores or processors, a bus, memory controller, cache, etc. A multi-core processor may be symmetric or asymmetric.

To enable user interaction with the computing device 700, an input device 745 can represent any number of input mechanisms, such as a microphone for speech, a touch-sensitive screen for gesture or graphical input, keyboard, mouse, motion input, speech and so forth. An output device 735 can also be one or more of a number of output mechanisms known to those of skill in the art. In some instances, multimodal systems can enable a user to provide multiple types of input to communicate with the computing device 700. The communications interface 740 can generally govern and manage the user input and system output.

There is no restriction on operating on any particular hardware arrangement and therefore the basic features here may easily be substituted for improved hardware or firmware arrangements as they are developed.

Storage device 730 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 725, read only memory (ROM) 700, and hybrids thereof.

The storage device 730 can include software modules 732, 734, 736 for controlling the processor 710. Other hardware or software modules are contemplated. The storage device 730 can be connected to the system bus 705. In one aspect, a hardware module that performs a particular function can include the software component stored in a computer-readable medium in connection with the necessary hardware components, such as the processor 710, bus 705, display 735, and so forth, to carry out the function.

Figure 7B:
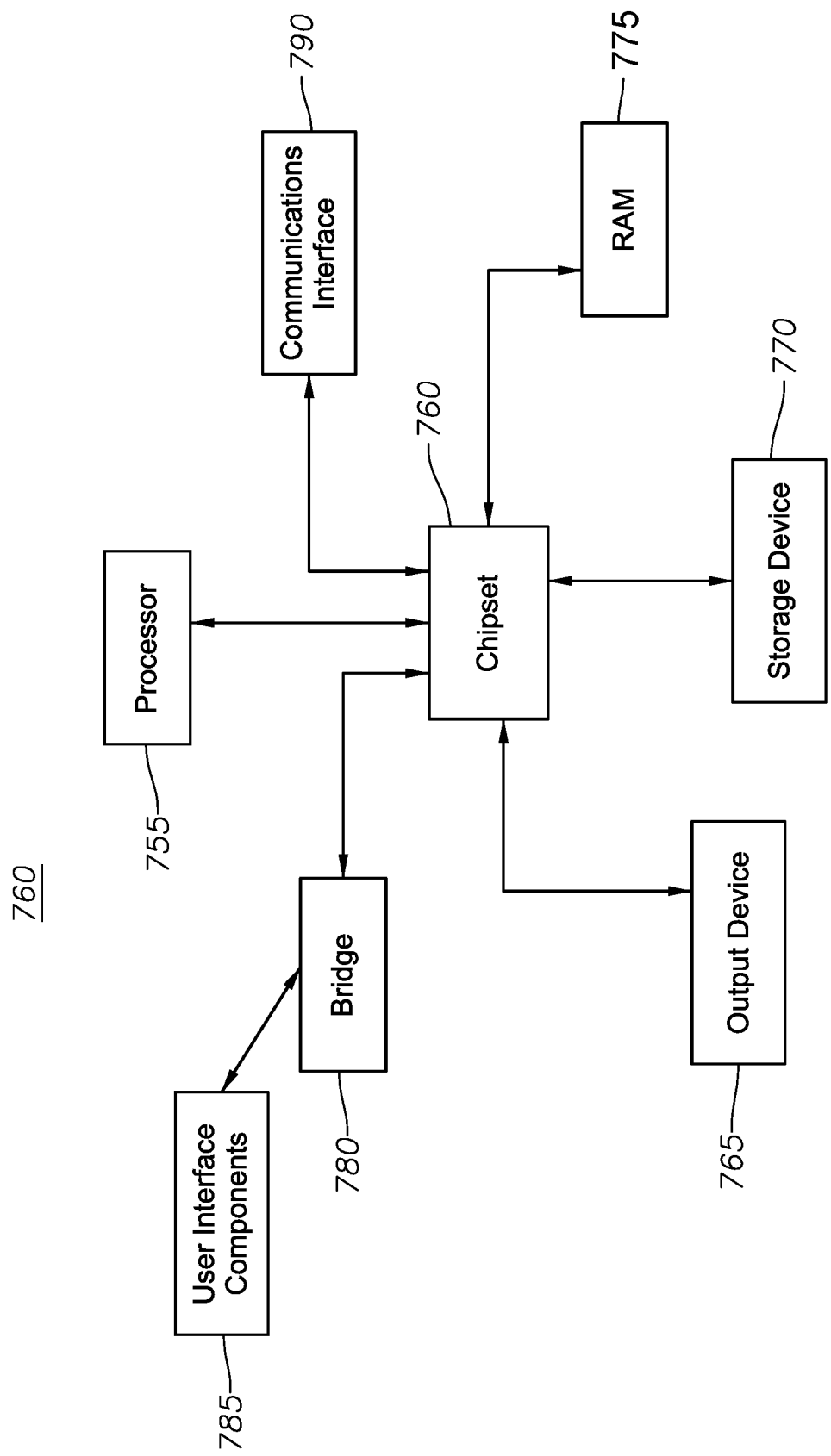

FIG. 7B illustrates a computer system 750 having a chipset architecture that can be used in executing the described method and generating and displaying a graphical user interface (GUI). Computer system 750 is an example of computer hardware, software, and firmware that can be used to implement the disclosed technology. System 750 can include a processor 755, representative of any number of physically and/or logically distinct resources capable of executing software, firmware, and hardware configured to perform identified computations. Processor 755 can communicate with a chipset 760 that can control input to and output from processor 755. In this example, chipset 760 outputs information to output 765, such as a display, and can read and write information to storage device 770, which can include magnetic media, and solid state media, for example. Chipset 760 can also read data from and write data to RAM 775. A bridge 780 for interfacing with a variety of user interface components 785 can be provided for interfacing with chipset 760. Such user interface components 785 can include a keyboard, a microphone, touch detection and processing circuitry, a pointing device, such as a mouse, and so on. In general, inputs to system 750 can come from any of a variety of sources, machine generated and/or human generated.

Chipset 760 can also interface with one or more communication interfaces 790 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 755 analyzing data stored in storage 770 or 775. Further, the machine can receive inputs from a user via user interface components 785 and execute appropriate functions, such as browsing functions by interpreting these inputs using processor 755.

It can be appreciated that exemplary systems 700 and 750 can have more than one processor 710 or be part of a group or cluster of computing devices networked together to provide greater processing capability.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. An apparatus enhancing the reliability of a pneumatically driven surgical tool, comprising:
 a source of regulated pneumatic pressure;
 an isolation valve fluidly coupled to the source of regulated pneumatic pressure and fluidly coupled to both a primary drive valve and a backup drive valve;
 a first circuit selection valve and a second circuit selection valve, each coupled with a respective first and second chamber of a surgical tool and coupled with both the primary drive valve and the backup drive valve;
 a first pressure sensor fluidly coupled between the first circuit selection valve and the first chamber of the surgical tool;
 a second pressure sensor fluidly coupled between the second circuit selection valve and the second chamber of the surgical tool; and
 a control system containing a processor and a non-transitory computer readable medium that contains instructions which, when executed by the processor, cause the processor to:

monitor the pneumatic pressure from the first pressure sensor and the second pressure sensor;

determine when the pneumatic pressure flowing through the first pressure sensor and the second pressure sensor is normal or abnormal;

actuate the isolation valve to selectively allow pneumatic pressure to flow to the primary drive valve and suppress pneumatic pressure to the backup drive valve and to suppress pneumatic pressure to flow to the primary drive valve and allow pneumatic pressure to the backup drive valve; and actuate the first and second circuit selection valves to selectively receive pneumatic pressure from the primary drive valve or the backup drive valve and to alternatively drive and vent the first chamber and the second chamber of the surgical tool regardless of whether the isolation valve allows the flow of pneumatic pressure through the primary drive valve or the backup drive valve.

2. The apparatus of claim 1, wherein the first chamber and the second chamber of the surgical tool is separated by a diaphragm connected to a cutting device, wherein the cutting device performs a cutting function when the diaphragm is actuated by pneumatic pressure alternatively driving and venting the first chamber and the second chamber.

3. The apparatus of claim 1, wherein the instructions further cause the processor to determine that the pneumatic pressure flowing through the first pressure sensor and the second pressure sensor is abnormal by determining when differential pressure between the first pressure sensor and the second pressure sensor is below a threshold value.

4. The apparatus of claim 1, wherein the instructions further cause the processor to apply a remediation step to return the differential pressure between the first pressure sensor and the second pressure sensor to exceed a threshold value after determining that the pneumatic pressure flowing through the first pressure sensor and the second pressure sensor is abnormal, wherein the remediation step is applied prior to actuating the isolation valve to suppressing pneumatic pressure to flow to the primary drive valve and allowing pneumatic pressure to the backup drive valve.

5. The apparatus of claim 4, wherein the remediation step comprises adjusting a valve duty cycle of the primary drive valve.

6. A method of enhancing the reliability of a pneumatically driven surgical tool, comprising:

monitoring, using one or more pressure sensors, a pneumatic pressure of a first fluidic line from first circuit selection valve and a second fluidic line from second circuit selection valve, wherein each of the first circuit selection valve and second circuit selection valve are coupled with a respective first and second chamber of a surgical tool and are respectively coupled with both a primary drive valve and a backup drive valve;

determining that the pneumatic pressure flowing through one or both of the first fluidic line and the second fluidic line is normal or abnormal;

determining when to switch to a backup drive valve mode by actuating an isolation valve to suppress pneumatic pressure flowing to the primary drive valve and allowing the pneumatic pressure to flow to the backup drive valve and actuating the first and second circuit selection valves to selectively receive pneumatic pressure from the backup drive valve and to alternatively drive and vent the first chamber and the second chamber of a surgical tool.

7. The method of claim 6, wherein the first chamber and the second chamber of the surgical tool is separated by a diaphragm connected to an cutting device, wherein the cutting device performs a cutting function when the diaphragm is actuated by pneumatic pressure alternatively driving and venting the first chamber and the second chamber.

8. The method of claim 6, wherein determining that the pneumatic pressure flowing through one or both of the first fluidic line and the second fluidic line is abnormal comprises determining when differential pressure between the first pressure sensor and the second pressure sensor is below a threshold value.

9. The method of claim 8, further comprising:

after determining that the pneumatic pressure flowing through one or both of the first fluidic line and the second fluidic line is abnormal and before actuating the isolation valve and the first and second circuit selection valves, applying a remediation step to return the differential pressure between the first pressure sensor and the second pressure sensor to exceed a threshold value.

10. The method of claim 9, wherein the remediation step comprises adjusting a valve duty cycle of the primary drive valve.

11. The method of claim 9, further comprising:

after determining, using the one or more pressure sensors, that the remediation step was not successful in returning the differential pressure between the first pressure sensor and the second pressure sensor to exceed the threshold value, actuating the isolation valve and the first and second circuit selection valves to allow the pneumatic pressure to flow to the backup drive valve and to alternatively drive and vent the first chamber and the second chamber of a surgical tool.

12. The method of claim 11, further comprising:

after actuating the isolation valve and the first and second circuit selection valves to allow the pneumatic pressure to flow to the backup drive valve and to alternatively drive and vent the first chamber and the second chamber of a surgical tool, monitoring, using the one or more pressure sensors, the pneumatic pressure of the first fluidic line from first circuit selection valve and the second fluidic line from the second circuit selection valve;

determining that the pneumatic pressure flowing through one or both of the first fluidic line and the second fluidic line is abnormal.

13. The method of claim 12, wherein determining that the pneumatic pressure flowing through one or both of the first fluidic line and the second fluidic line is abnormal comprises determining when differential pressure between the first pressure sensor and the second pressure sensor is below a threshold value.

14. The method of claim 13, further comprising after determining that the pneumatic pressure flowing through one or both of the first fluidic line and the second fluidic line is abnormal, applying the remediation step to return the differential pressure between the first pressure sensor and the second pressure sensor to exceed a threshold value.

15. The method of claim 14, further comprising:

after determining, using the one or more pressure sensors, that the remediation step was not successful in returning the differential pressure between the first pressure sensor and the second pressure sensor to exceed the threshold value, actuating the isolation valve, the primary drive valve, the backup drive valve, and the first and second circuit selection valves to terminate operation of the surgical tool.

16. A non-transitory computer readable medium that contains instructions which, when executed by a processor, cause the processor to:

monitor, using one or more pressure sensors, a pneumatic pressure of a first fluidic line from first circuit selection valve and a second fluidic line from second circuit selection valve, wherein each of the first circuit selection valve and second circuit selection valve are coupled with a respective first and second chamber of a surgical tool and are respectively coupled with both a primary drive valve and a backup drive valve;

determine when the pneumatic pressure flowing through one or both of the first fluidic line and the second fluidic line is normal or abnormal;

determine when to switch to a backup drive valve by actuating an isolation valve to suppress pneumatic pressure flowing to the primary drive valve and allowing the pneumatic pressure to flow to the backup drive valve and actuating the first and second circuit selection valves to selectively receive pneumatic pressure from the backup drive valve and to alternatively drive and vent the first chamber and the second chamber of a surgical tool.

17. The computer readable medium of claim 16, containing further instructions which, when executed by the processor, cause the processor to:

after determining that the pneumatic pressure flowing through one or both of the first fluidic line and the second fluidic line is abnormal and before actuating the isolation valve and the first and second circuit selection valves, apply a remediation step to return the pneumatic pressure of the first fluidic line and the second fluidic line to normal values.

18. The computer readable medium of claim 17, wherein the remediation step comprises adjusting a valve duty cycle of the primary drive valve.

19. The computer readable medium of claim 17, containing further instructions which, when executed by the processor, cause the processor to:

after determining, using the one or more pressure sensors, that the remediation step was not successful, actuate the isolation valve and the first and second circuit selection valves to allow the pneumatic pressure to flow to the backup drive valve and to alternatively drive and vent the first chamber and the second chamber of a surgical tool.

20. The computer readable medium of claim 19, containing further instructions which, when executed by the processor, cause the processor to:

after actuating the isolation valve and the first and second circuit selection valves to allow the pneumatic pressure to flow to the backup drive valve and to alternatively drive and vent the first chamber and the second chamber of a surgical tool:

monitor; using the one or more pressure sensors, the pneumatic pressure of the first fluidic line from first circuit selection valve and the second fluidic line from the second circuit selection valve;

determine that the pneumatic pressure flowing through one or both of the first fluidic line and the second fluidic line is abnormal;

apply an additional remediation step to return the pneumatic pressure of the first fluidic line and the second fluidic line to normal values;

determine, using the one or more pressure sensors, that the additional remediation step was not successful; and actuate the isolation valve, the primary drive valve, the backup drive valve, and the first and second circuit selection valves to terminate operation of the surgical tool.

* * * * *